US00PP08838P

United States Patent [19]

Austin

[11] Patent Number: Plant 8,838

[45] Date of Patent: Jul. 19, 1994

[54] ROSE PLANT AUSBURTON

[75] Inventor: David C. H. Austin, Albrighton, England

[73] Assignee: David Austin Roses Limited, Albrighton, England

[21] Appl. No.: 40,156

[22] Filed: Mar. 29, 1993

[51] Int. Cl.[5] ..... A01H 5/00

[52] U.S. Cl. ..... Plt./1

[58] Field of Search ..... Plt. 1

*Primary Examiner*—James R. Feyrer
*Attorney, Agent, or Firm*—Klarquist Sparkman Campbell Leigh & Whinston

[57] ABSTRACT

A *Rosa hybrida shrub rose plant is disclosed having fully double flowers, soft pink flower color, strong fragrance and reflexed character of outer petals.*

1 Drawing Sheet

The present invention relates to a new and distinct variety of rose plant (*Rosa hybrida*) of the shrub class which was originated by me by crossing the unpatented variety "The Prioress" with the unpatented variety "Mary Rose".

The primary objective of this breeding was to produce a new rose variety having repeat flowering and pink, old-fashioned-type flowers. The objective was substantially achieved along with other desirable improvements as evidenced by the following unique combination of characteristics which are outstanding in the new variety and which distinguish it from its parents, as well as from all other varieties of which I am aware:

1. Fully double flowers;
2. Soft pink color flowers;
3. Strong fragrance; and
4. Outer petal reflex.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—"The Prioress" variety.

*Pollen parent.*—"Mary Rose" variety.

classification:

*Botanical.*—*Rosa hybrida.*

*Commercial.*—Shrub.

FLOWER

Observations made from specimens grown in a garden environment in Albrighton, wolverhampton, England, in July, 1992.

Blooming habit: Recurrent.

Bud:

*Size.*—About 1.5–2.0 cm long when the petals start to unfurl.

*Form.*—Short, globular, broad based.

Color.—When sepals first divide, bud color is Grey-Purple Group 185B. When half blown, the upper sides of the petals are Red Group 49D. but paler; and the lower sides of the petals are Red Group 49D.

*Sepals.*—Color: Yellow-Green Group 144A/B with reddish blush. Surface texture: Glandular. Occasionally, sepals may be profoundly folitate. There are three normally to heavily appendaged sepals. There are two unappendaged sepals with smooth , downy edges.

*Receptacle.*—Color: Yellow-Green Group 144A. Shape: Funnel. Size: About 6–8 mm long×8–10 mm wide. Surface: Glandular.

*Peduncle.*—Length: Averaging about 3–4.5 cm. Surface: Glandular. Color: Light green, bronzy. Strength: Bending.

Bloom:

*Size.*—Medium. Average open size is 7.5 cm.

Borne.—Several together, in clusters having irregular shape.

*Stems.*—Medium length, normal strength. Average length is about 50–60 cm.

*Form.*—When first open: Cupped. Permanence: Flattens slightly; outer petals curl back. Inner petals appear cramped and tend to be caught into the calyx to form a button.

*Petalage.*—Number of petals under normal conditions 140 ranging from 130 to 150, the number and size of petals decreasing slightly as the season progresses. Petaloids are not formed.

*Color.*—The upper side of the petals is Between Red Group 36D and Orange Group 27D, very pale, with some deeper coloring on outer petals Red Group 56B. The reverse side of the petals is Yellow-Orange Group 19D, but paler. The base of the petals is Yellow-Orange Group 19D from center to base, with darker yellow (Yellow Group 11A/B) at the tip. The major color on the upper side is Red Group 36D, but paler.

*Variegations.*—None.

*Discoloration.*—The general tonality at the end of the first day: Petal color slightly paler. At the end of the third day: Petals less pink and less yellow, almost white.

*Fragrance.*—Moderate to strong, sweet.

Petals:

*Texture.*—Leathery on medium petals.

*Shape.*—Round, notched at apex, cupped. Outer petals wide, heart shaped.

*Form.*—Edges slightly quilled.

*Arrangement.*—Slightly quartered at center, outside imbricated, with many petaloids in the center.

*Persistence.*—Outer petals drop off cleanly before drying. Inner petals hang on and dry.

*Lastingness.*—On the plant: About 3 days. As a cut flower: About 3 days.

Reproductive parts:

*Anthers.*—Size: Medium. Quantity: Very few. Color: Yellow. Arrangement: Mixed with petaloids.

*Filaments.*—Color: White.

*Pollen.*—Color: Gold yellow.

*Styles.*—Color: White to very pale green. Inner styles tend to be foliate.

*Stigmas.*—Color: Yellow.

Form.—Shrub.

*Fertility.*—The flowers are sterile. The styles and stigmas are visible, but not the stamens. Hips do not form under normal conditions at the site of the observations.

Growth: Medium vigor, branching basally dominant with 6 to 8 strong canes. The internode spacing is about 4 cm, and the plant has a canopy of medium density. The mature plant is about 76 cm tall and 60 cm wide.

Foliage:

*Number of leaflets on normal mid-stem leaves.*—5.

*Size.*—Medium large, about 17–18 cm long × 14–15 cm wide.

*Quantity.*—Normal.

*Color.*—New foliage: Yellow-Green Group 144A with reddish blush on margins and veins. Old foliage: Yellow-Green Group 147A.

Leaflets:

*Shape.*—Pointed oval.

*Texture.*—Upper side: Leathery.

*Edge.*—Serrated.

*Serration.*—Double, small.

*Petiole rachis.*—Color: Green.

*Petiole underside.*—Glandular, with prickles (2.5 prickles per internode).

*Stipules.*—About 2.5–3.0 cm long.

*Disease resistance.*—Resistant to mildew and blackspot under normal growing conditions at Albrighton, Wolverhampton, England.

Wood:

*New wood.*—Color: Dark green, reddish. Bark: Smooth.

*Old wood.*—Color: Green, streaky. Bark: Smooth.

Prickles:

*Quantity.*—Many (3 to 5 per internode, each 4 to 5 mm long) on main canes from base with numerous very small thorns, less than 1 mm long. Ordinary number on laterals from main canes.

*Form.*—Medium length, hooked downward.

*Color when young.*—Green and red.

Small prickles:

*Quantity.*—Many on main stalks and on laterals.

*Color.*—Brown.

*Position.*—Evenly distributed around stem.

I claim:

1. A new and distinct variety of *Rosa hybrida* rose plant of the shrub class, substantially as herein shown and described, characterized particularly as to novelty by the unique combination of its fully double flowers, soft pink flower color, strong fragrance, and reflexed character of outer petals.

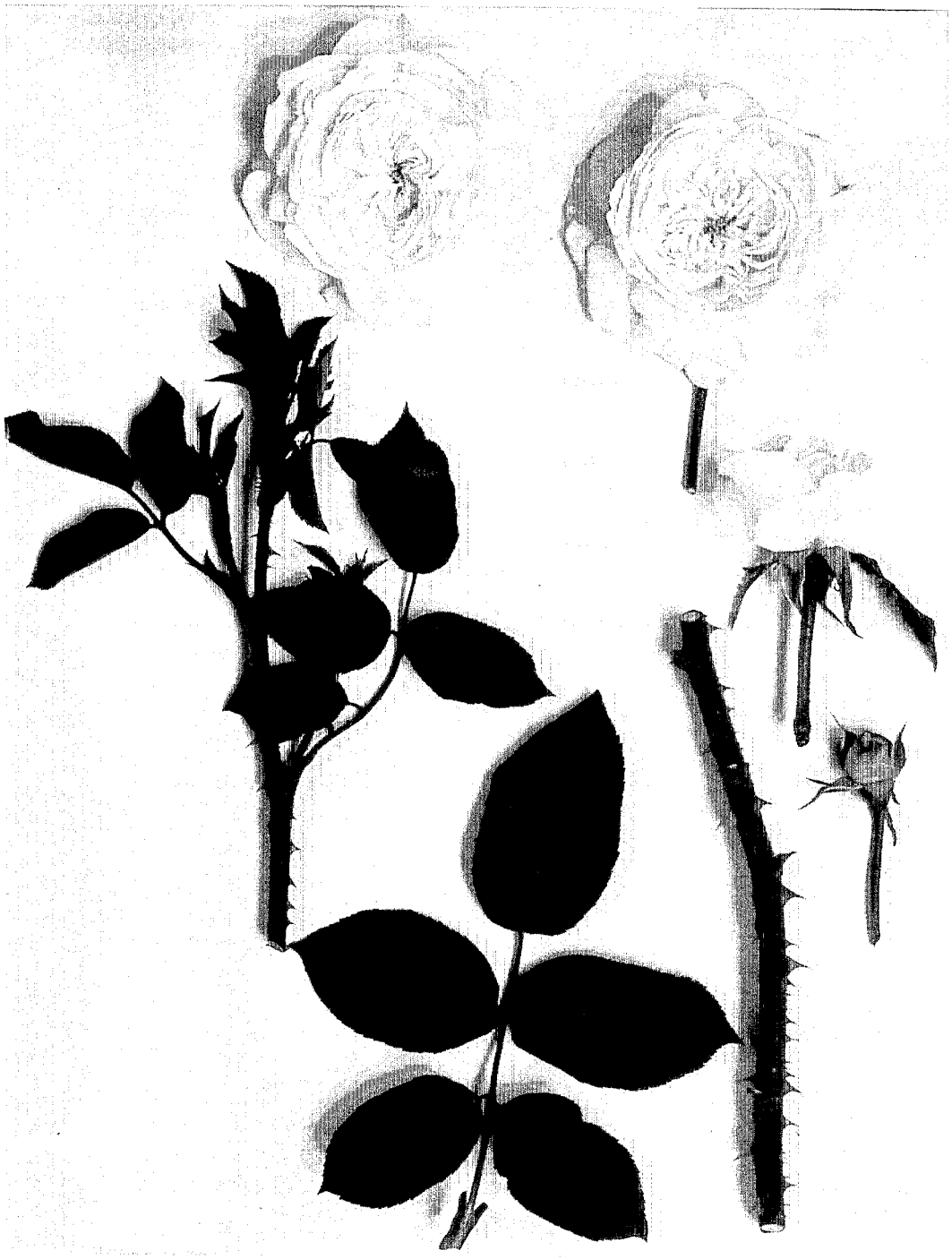

* * * * *